United States Patent [19]
Bernes et al.

[11] Patent Number: 5,270,003
[45] Date of Patent: Dec. 14, 1993

[54] BLOOD SAMPLING SYSTEM

[75] Inventors: Jean-Claude Bernes, Faimes; Michel Joie, Ernage; Baudouin Vanbreedam, Heverlee; Jean-Marie Mathias, Lillois; Jean-Marc Payrat, Nivelles, all of Belgium

[73] Assignee: Baxter International Inc., Deerfield, Ill.

[21] Appl. No.: 979,145

[22] Filed: Nov. 20, 1992

[51] Int. Cl.⁵ .................. A61M 5/14; A61M 39/02; A61M 5/32
[52] U.S. Cl. .................. 422/44; 422/99; 436/810; 435/296; 604/4; 604/7; 604/178; 604/250; 604/403; 604/905
[58] Field of Search .......... 422/44, 99; 436/810; 435/296; 604/4, 7, 403, 905, 192, 198, 250, 280, 282, 283, 177, 178; 285/319, 921

[56] References Cited

U.S. PATENT DOCUMENTS

| | | | |
|---|---|---|---|
| 4,643,711 | 2/1987 | Bates | 604/4 |
| 4,655,764 | 4/1987 | Sato | 604/905 X |
| 4,911,696 | 3/1990 | Miyasaka et al. | 604/244 |
| 5,045,067 | 9/1991 | Ohnaka et al. | 604/244 |
| 5,122,129 | 6/1992 | Olson et al. | 604/905 |

Primary Examiner—Robert J. Warden
Assistant Examiner—E. Leigh Dawson

[57] ABSTRACT

A blood sampling system having an in-line sampling member is provided. The member includes a frangible joint located along the length thereof providing an easily openable port for directly sampling a donor's blood during blood collection into a collection bag. In further embodiments, an integral clamping system can be provided with the sampling member for temporarily cutting off flow of blood from a donor.

16 Claims, 8 Drawing Sheets

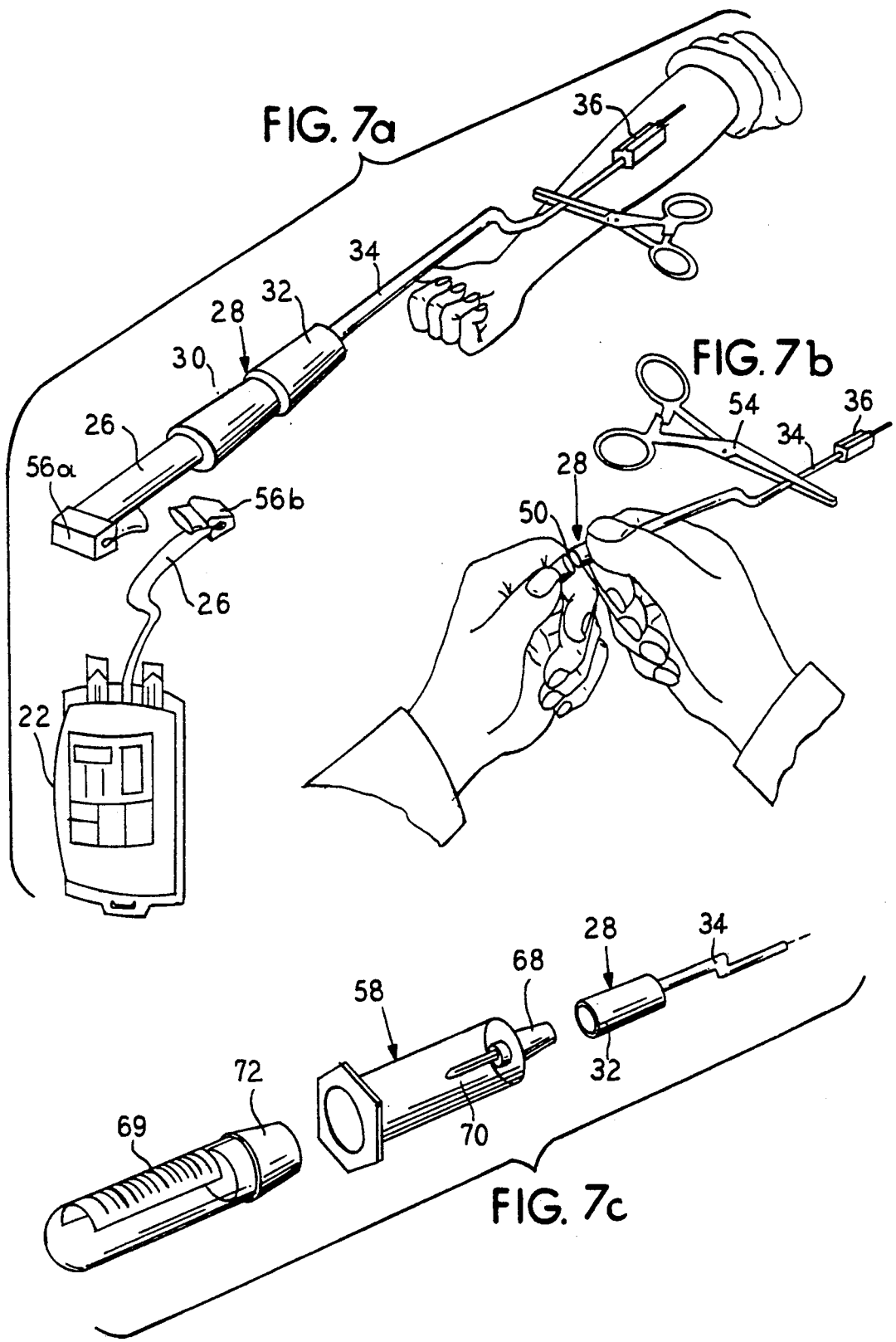

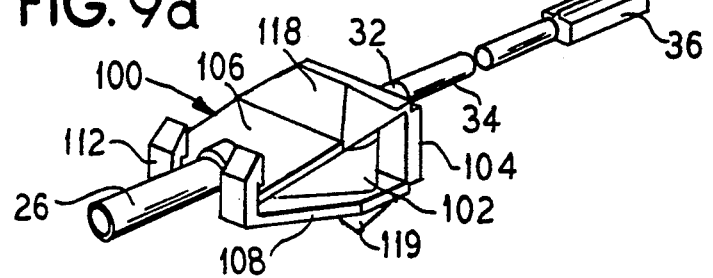
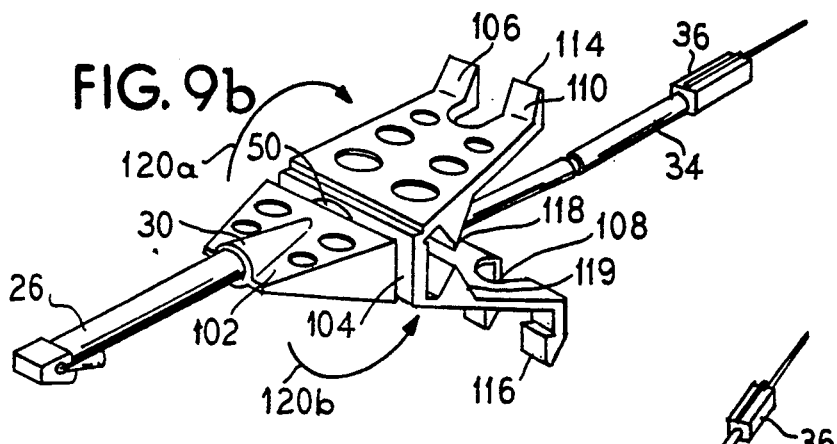
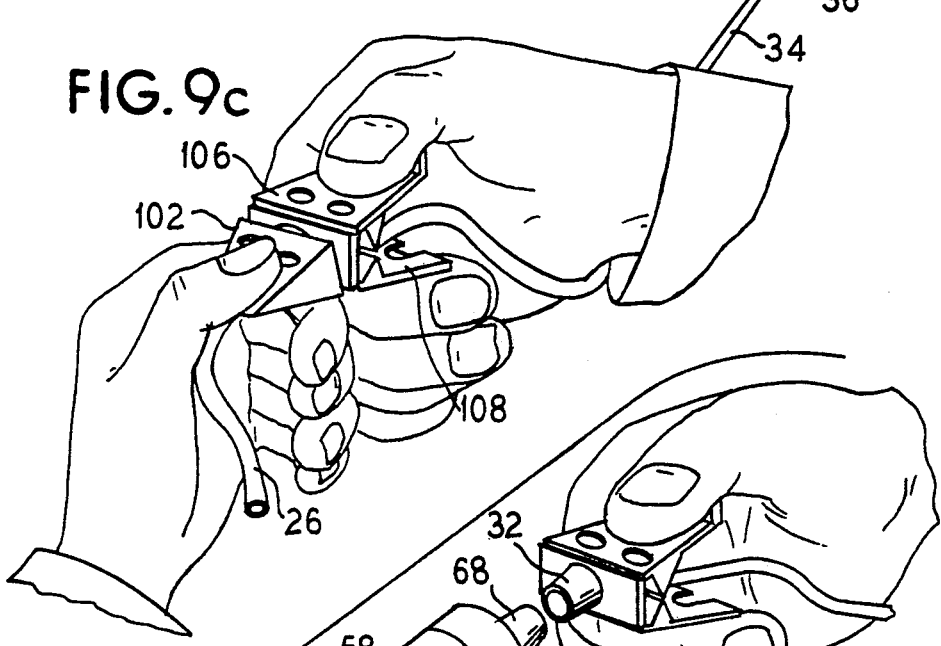
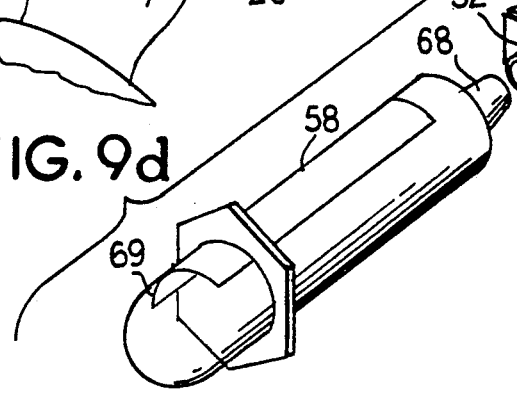

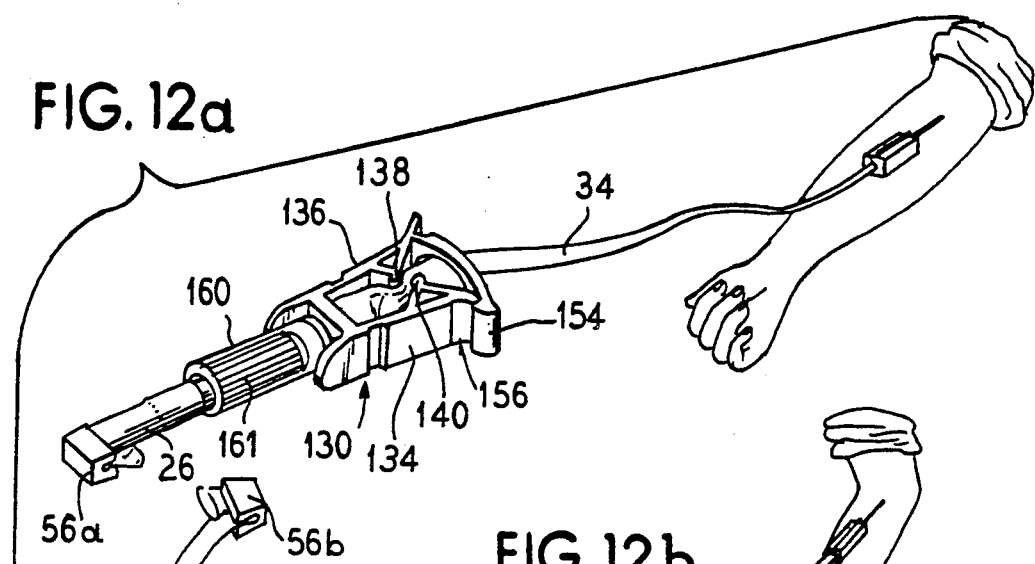
FIG. 12a
FIG. 12b
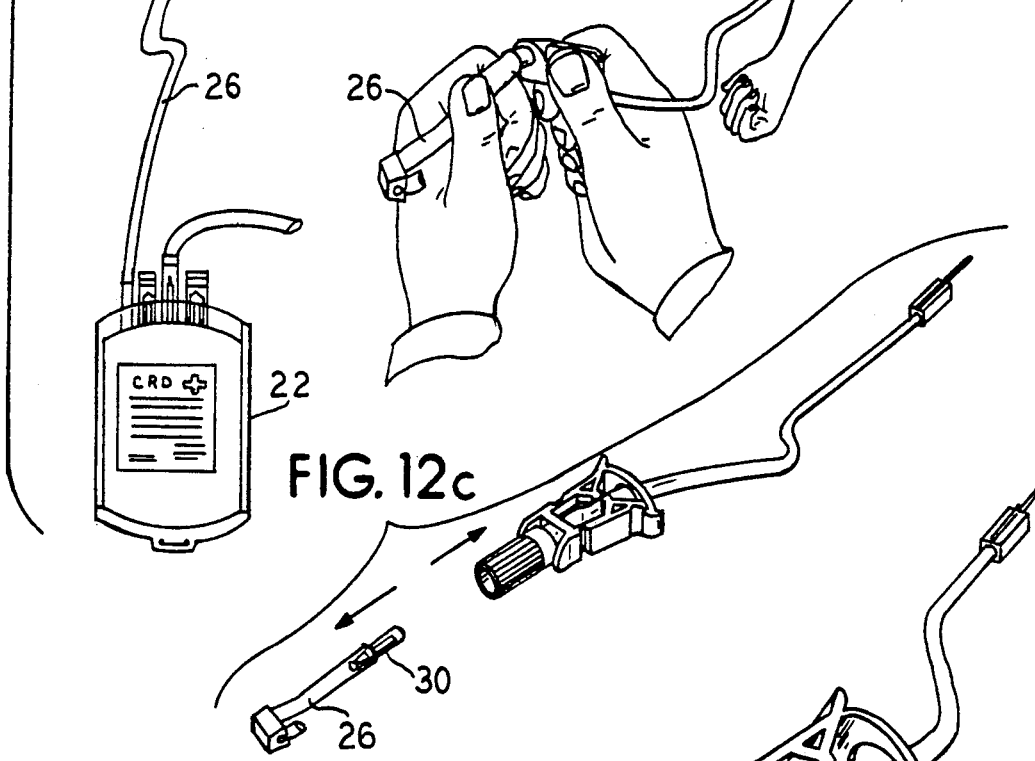
FIG. 12c
FIG. 12d
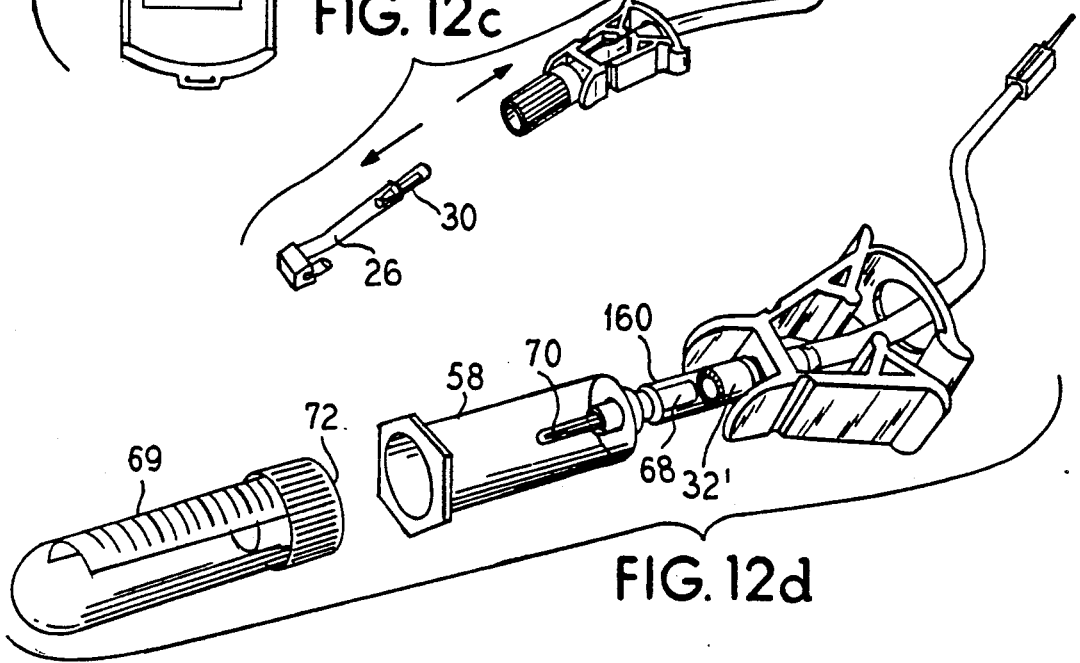

BLOOD SAMPLING SYSTEM

BACKGROUND OF THE INVENTION

The present invention relates to blood collection and sampling systems generally. More specifically, the present invention relates to systems for sampling blood directly from a donor during the collection process.

Of course, it is known to collect and use blood for a variety of treatments and therapies, e.g., transfusions. To effectively use collected blood it is necessary to test the blood to determine its type and other characteristics.

It is advantageous to sample blood directly from a donor rather than sample blood that is collected in a collection bag. An anticoagulant, or other solutions, are typically added to the blood in the collection bag. By sampling directly from the donor, undiluted blood, e.g., blood with no anticoagulant or other constituent, from the donor can be sampled.

A variety of techniques are used for this type of blood sampling. Such techniques are illustrated in FIGS. 1-4.

In one technique illustrated in FIG. 1, a tube 10 leading from a donor needle 11 to the primary collection bag (not illustrated) is clamped. Scissors are used to cut the tube on the collection bag side. The open end 12 of the tube 10 is then directed into a test tube 13 while releasing pressure on the clamp 14 to pour blood into the open test tube.

Another technique, illustrated in FIG. 2, utilizes an in-line intermediate needle 16 that is exposed by removing an in-line cover section 15 of the tube. An evacuated donor sampling tube 17 with a rubber stopper is connected to the needle 16. The needle 16 pierces the rubber stopper and blood flows into the sampling tube 17.

FIG. 3 illustrates another method of sampling blood. After the needle 18 is withdrawn from the donor's arm, the donor needle is used to pierce a rubber stopper of an evacuated test tube 19. A disadvantage of this system is that it does not sample blood from the donor but rather, samples blood, including an anticoagulant, from the primary collection bag 21.

FIG. 4 illustrates a still further method that involves using a Y-shaped branch connector 23 on the donor line 25 between the donor needle 27 and the primary collection bag (not shown). The outlet 33 of the Y connector includes a connection system allowing filling of an evacuated test tube 35 through an adaptor 37.

There are a number of disadvantages with the prior art systems. For example, the use of scissors to cut the tubes creates the possibility for contamination of the system. Further, the prior art techniques that require the use of a needle add the potential risk of accidental needle sticks. Still further, some of the prior systems had the potential that sterility of the process could be compromised.

There is therefore a need for an improved method for sampling blood directly from the donor.

SUMMARY OF THE INVENTION

The present invention provides a system for allowing the sampling of undiluted blood from a donor. The system includes means for opening the blood collection system and allowing blood sampling either directly into an open test tube or other means. The system can include a clamp allowing clamping of the donor tube during sticking of the donor and also clamping of the tube before opening the circuit for sampling the blood.

The present invention provides a blood sampling system that is safe and easy to use.

Pursuant to the present invention, a sampling member is provided that is in fluid communication with the collection needle; the needle being connected to a collection tube leading to a blood collection bag. The sampling member comprises a tubular member connected in-line with the collection tube. The tubular member includes a frangible joint for separating the tubular member into two pieces. The sampling member can include an integral clamp for temporarily clamping off blood flow in the tube adjacent the frangible joint.

The tubular member has a reduced diameter at the frangible joint which when bent and broken separates the member into two pieces. The piece connected by the tube to the donor needle can have a conical female luer connection which is exposed by the breaking of the frangible joint. By clamping the tube between the donor needle and the member and breaking the member at the frangible joint, blood can be collected and sampled directly from the donor.

In another embodiment, the tubular member is provided with laterally outwardly extending wings which provide for ease of handling and manipulating especially during the separating of the frangible joint.

In a further embodiment, a fold-over dual purpose clamp is formed with the tubular member. In one position, the clamp has hinged fork levers which have inwardly directed anvil pieces which can be squeezed together with the collection tube therebetween, to shut off flow. The frangible joint can thereafter be broken. In a second position, the fork levers can be arranged spanning across the frangible joint to reinforce the joint to prevent inadvertent breaking. The fork levers, in the second position, can be locked together.

In a still further embodiment, a clamp is formed with the tubular member and provides two pivotably flexible wall portions arranged on opposite sides of the collection tube, the wall portion having rounded bars which act as anvils for squeezing the collection tube to block flow when the wall portions are squeezed together. One of the wall portions provides a back wall which engages with the respective other wall portion to lock the wall portions squeezed together.

A bushing can be provided overlying and surrounding the frangible joint. When the clamp is locked together and the flow is cut off from the donor needle, the joint is separated and one side of the tubular member is removed. The thus overhanging bushing creates a female port for receiving a male luer connection.

An advantage of the present invention in that it provides systems which allow a quick, safe method of sampling blood.

Furthermore, an advantage of the present is that it provides a system for sampling blood directly from the donor.

Additionally, an advantage of the present invention is that it provides easy access to the blood flow through a frangible joint without the need for scissors.

Moreover, an advantage of the present invention is that it provides a frangible joint that is designed to fit directly with a luer connector allowing the direct use of an evacuated tube holder system while still being compatible with the use of open test tubes.

Still further, an advantage of the present invention is that it eliminates the risk of accidental needle sticks.

And further, an advantage of the present invention is that the blood donation is isolated before opening the collection system.

Additional features and advantages of the present invention are described in, and will be apparent from, the detailed description of the presently preferred embodiments and from the drawings.

BRIEF DESCRIPTION OF THE DRAWINGS

FIG. 7a is an exploded perspective view of the present invention;

FIG. 7b is a perspective view of a second stage of operation of the present invention;

FIG. 7c is an exploded perspective view of a third stage of the operation of the present invention;

FIG. 9a is a perspective view of a further embodiment of the sampling member of the present invention;

FIG. 9b is a perspective view of a second stage of manipulation of the sampling member of FIG. 9a;

FIG. 9c is a perspective view of the sampling member of FIG. 9b and a further stage of manipulation;

FIG. 9d is an exploded perspective view of the sampling member of FIG. 9c in a still further stage of manipulation;

FIG. 12a is an exploded perspective view of a system using the sampling member of FIG. 10;

FIG. 12b is a perspective view of the system of FIG. 12a in a further stage of manipulation;

FIG. 12c is an exploded perspective view of the system of FIG. 12a in a still further stage of manipulation; and FIG. 12d is an exploded perspective view of the system of FIG. 12a in a still further stage of manipulation.

DETAILED DESCRIPTION OF THE PRESENTLY PREFERRED EMBODIMENTS

The present invention provides improved apparatus and methods for sampling blood during the collection process. FIGS. 1-4 illustrate prior art methods of sampling blood, as described in the Background of the Invention. The present invention provides improved systems and methods over these prior art systems.

Figure 1:
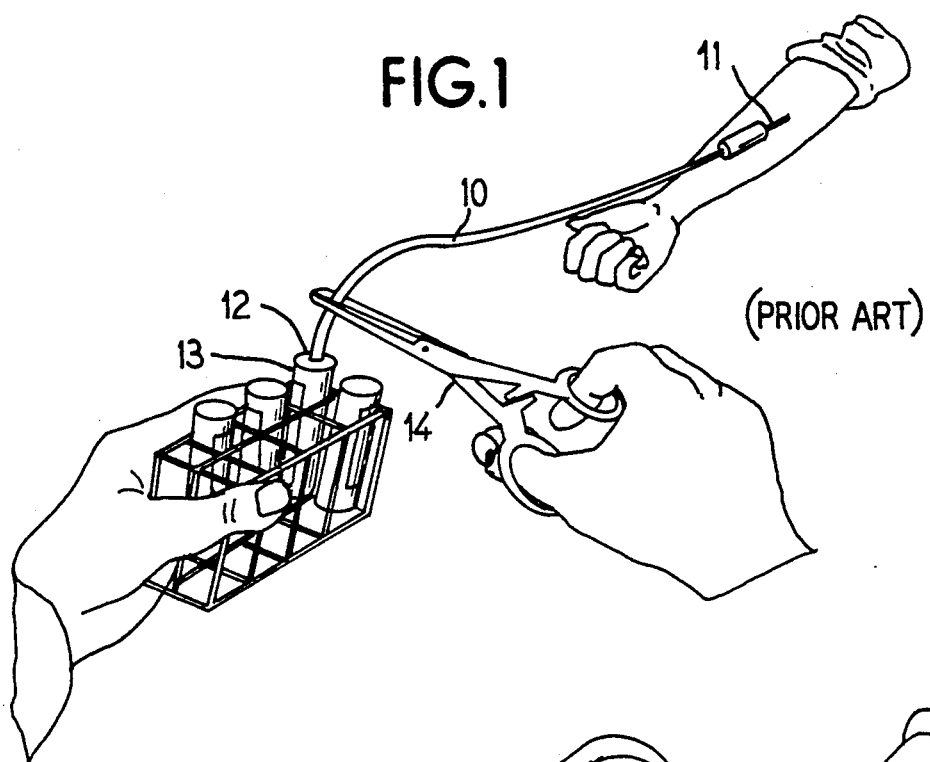
FIG. 1 is a perspective view of a prior art arrangement for sampling blood.
Figure 2:
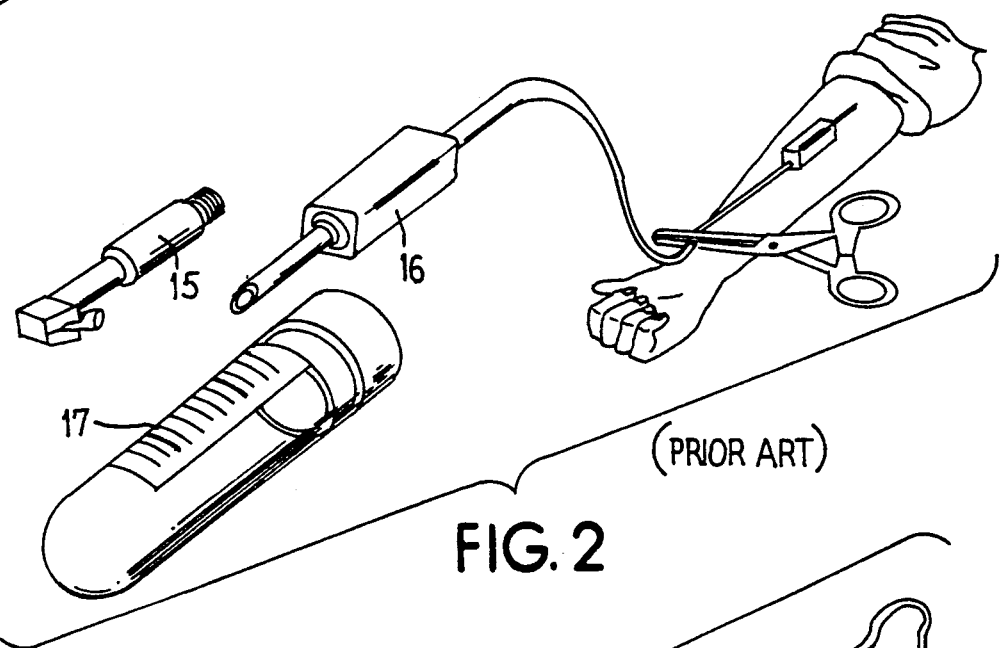
FIG. 2 is an exploded view of another prior art system for sampling blood.
Figure 3:
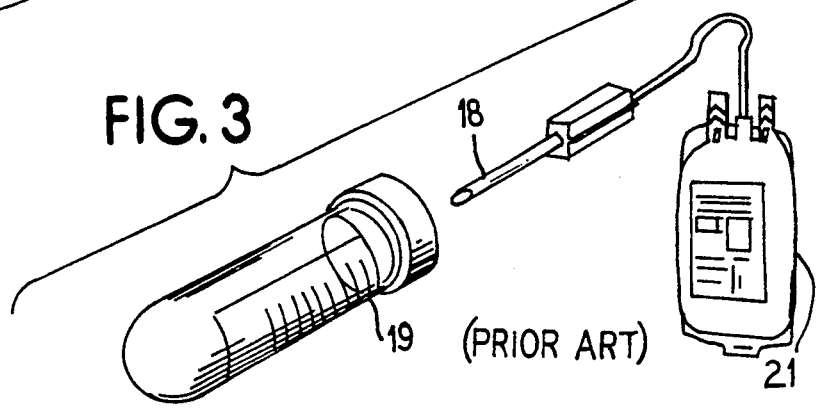
FIG. 3 is an exploded view of a third prior art system for sampling blood.
Figure 4:
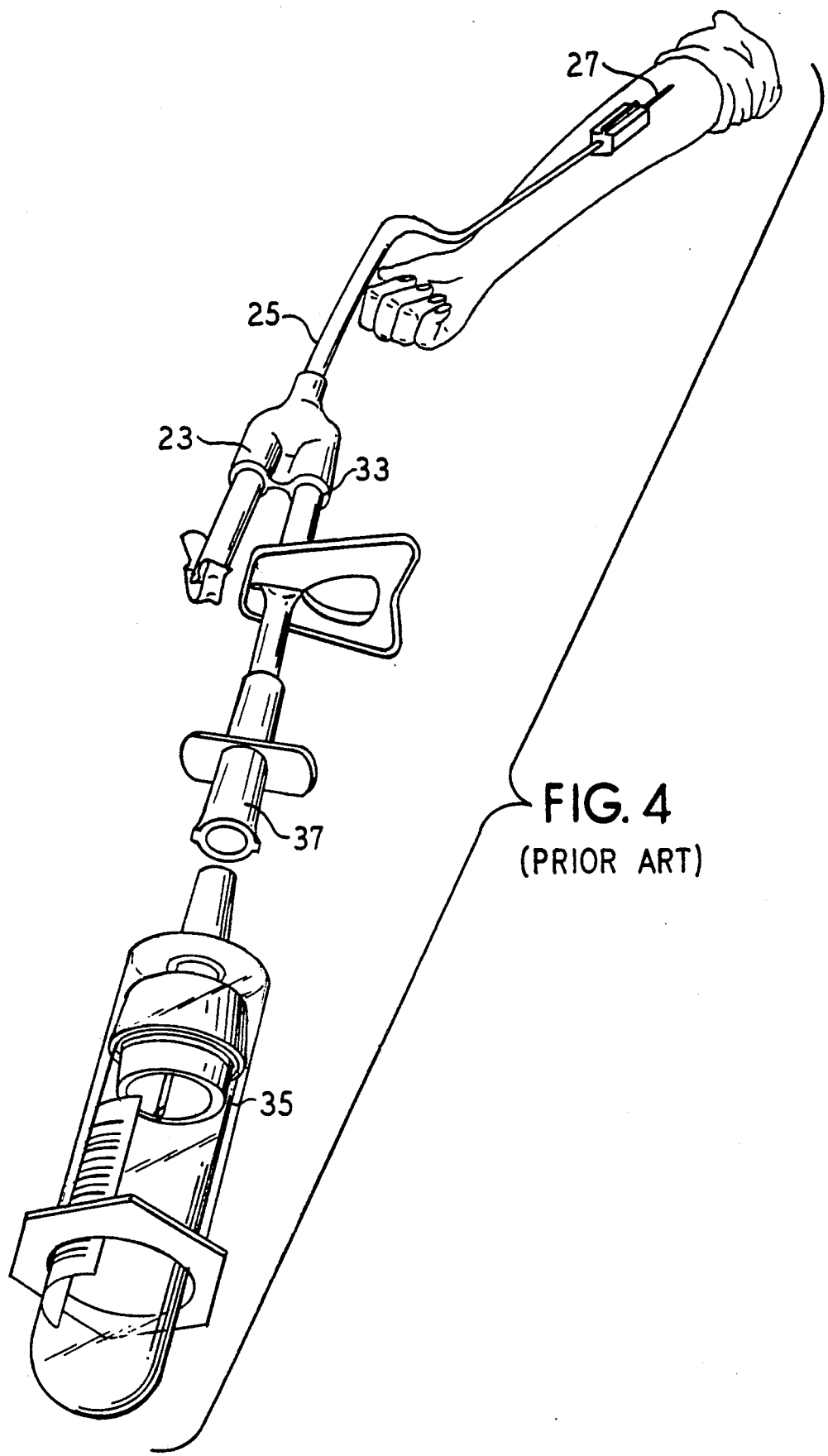
FIG. 4 is an exploded view of still another prior art system for sampling blood.
Figure 5:
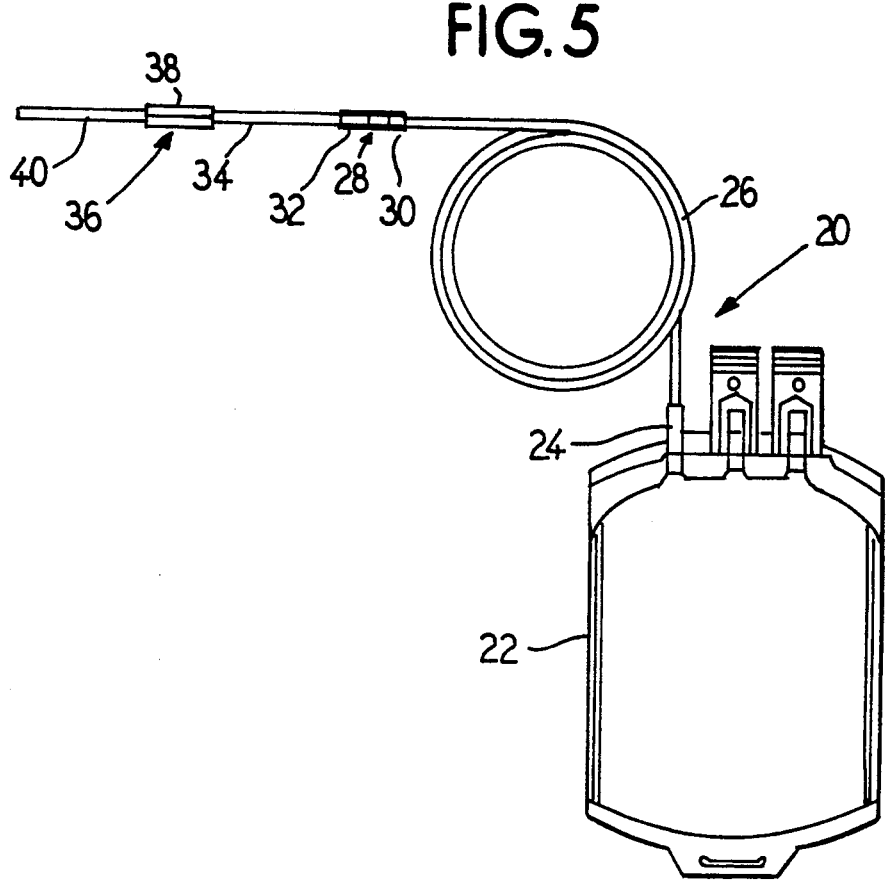
FIG. 5 is an elevational view of an embodiment of the present invention.

Referring now to FIG. 5, an embodiment of a sampling system 20 of the present invention is illustrated. The sampling system includes a collection container 22 having an inlet port 24 connected to a donor tube 26 which is connected to a sampling member 28 of the present invention. The sampling member 28 comprises a first section 30 connected to a second section 32 in axial flow-through alignment. The second section 32 is connected to a sample tube 34 which is itself connected to a donor needle 36. The donor needle 36 includes a tube member 38 and a sticking needle 40 that is inserted into a donor.

Figure 6:
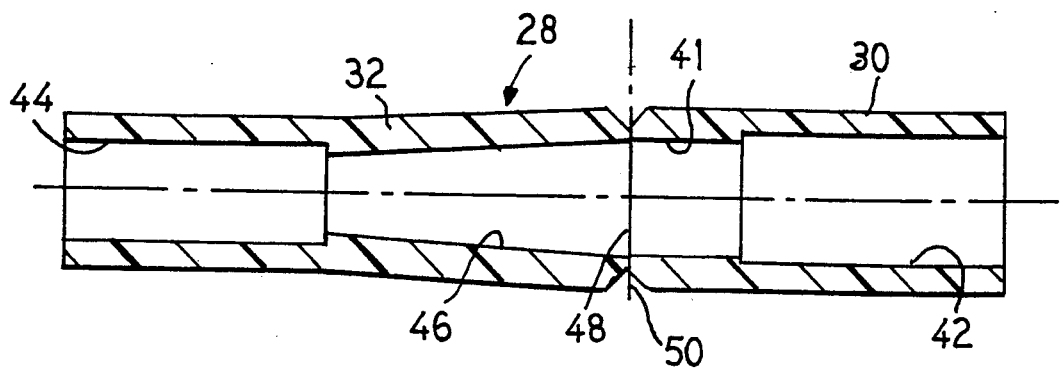
FIG. 6 is a longitudinal sectional view of an embodiment of the sampling member of the present invention.

FIG. 6 illustrates the sampling member 28 in more detail. A central flow-through channel 41 extends through the first section 30 and the second section 32. The first section 30 has a female socket 42 for holding the donor tube 26 therein. The first section 30 can also be sized to hold the donor tube around an outer diameter thereof.

The second section 32 includes a second female socket 44 for holding the sample tube 34 therein. The second section 32 can also be sized to hold the sample tube 34 around an outer diameter thereof.

In a center section of the sampling member 28, in particular in the second section 32, is a conical socket 46 expanding to a dividing line 48 between the second section 32 and the first section 30. At the dividing line 48 the outside diameter of the member 28 is preferably reduced by an annular notch 50. This creates a frangible joint between the first section 30 and the second section 32. The conical port 46 is shaped and adapted to the dimensions of a female luer connection.

FIGS. 7a through 7b illustrate the operation of the sampling system 20. A clamping system 54 is placed onto the sample tube 34 between the donor needle 36 and the sampling member 28. Although clamp 54 is used in the illustrated embodiment, if desired, other clamp mechanisms can be used to stop the flow through the donor tube 26.

After the tube is clamped, the donor tube 26 is cut. The clamps 56a, 56b isolate the collection bag 22 from the donor tube 26 adjacent the sample member 28.

As illustrated in FIG. 7b, the sampling member 28 is then broken at the notch 50 by a bending movement In the preferred embodiment, as illustrated in FIG. 7c, a tube holder including a luer 58 is then inserted into the second section 32 of the sample member 28, particularly a male luer nozzle 68 is inserted into the conical socket 46. A sample tube 69 is inserted into the tube holder 58 wherein a needle 70 pierces a rubber stopper 72 covering the sample tube 69.

The clamp 54 is then released from the donor tube 26 and blood flows from the donor's arm through the sample tube 34. The blood flows through the second section 32, through the male luer nozzle 68 and the needle 70, which pierces the rubber stopper 72, and into the sample tube 69.

Figure 8A:
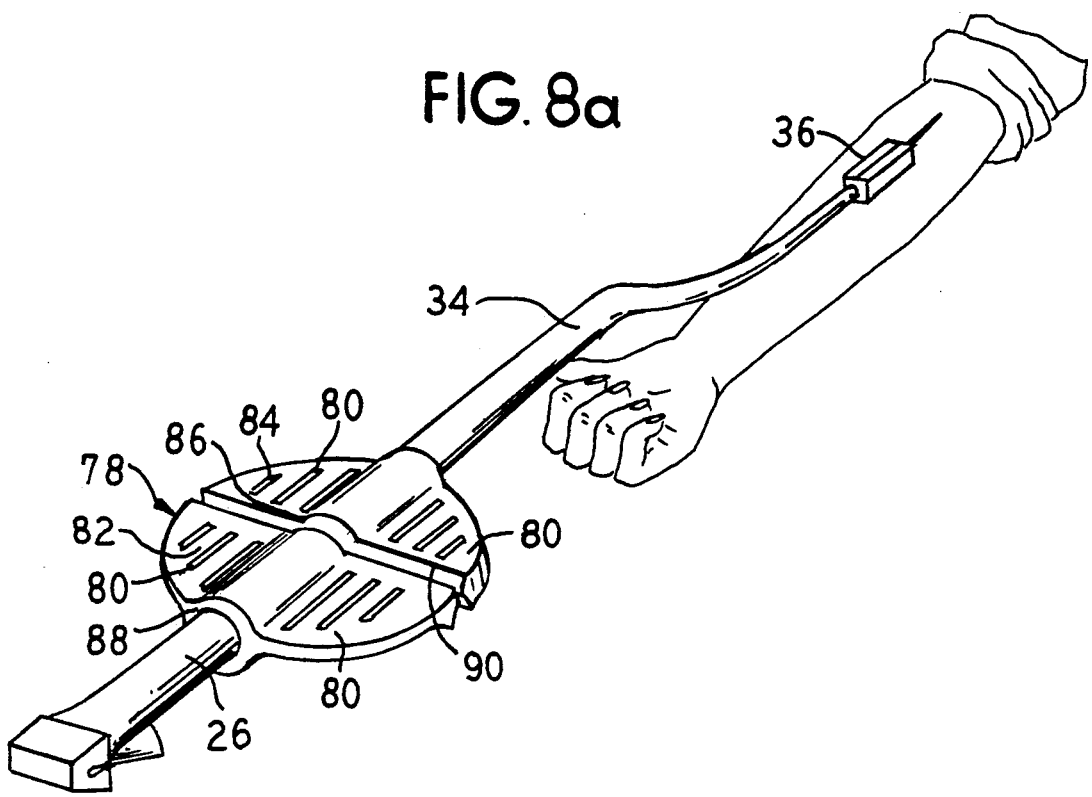
FIG. 8a is a perspective view of another embodiment of the sampling member of the present invention.

FIG. 8a illustrates another embodiment of the sampling member 78. In this embodiment the sampling member 78 is in other respects identical to the sampling member 28 except for outwardly disposed wings 80 on both a first tube section 82 and a second tube section 84. A notch 86 is arranged around an outer circumference of a central channel 88 similar to the notch 50 around the outer circumference of the central channel 41 of FIG. 6. The wings 80 are separated by a through-gap 90 across a distance between the first tube section 82 and the second tube section 84. Alternately, the notch 86 can be formed around the entire outer perimeter of both the channel 88 and the wings 80 wherein no through gap 90 would be provided between the wings.

Figure 8B:
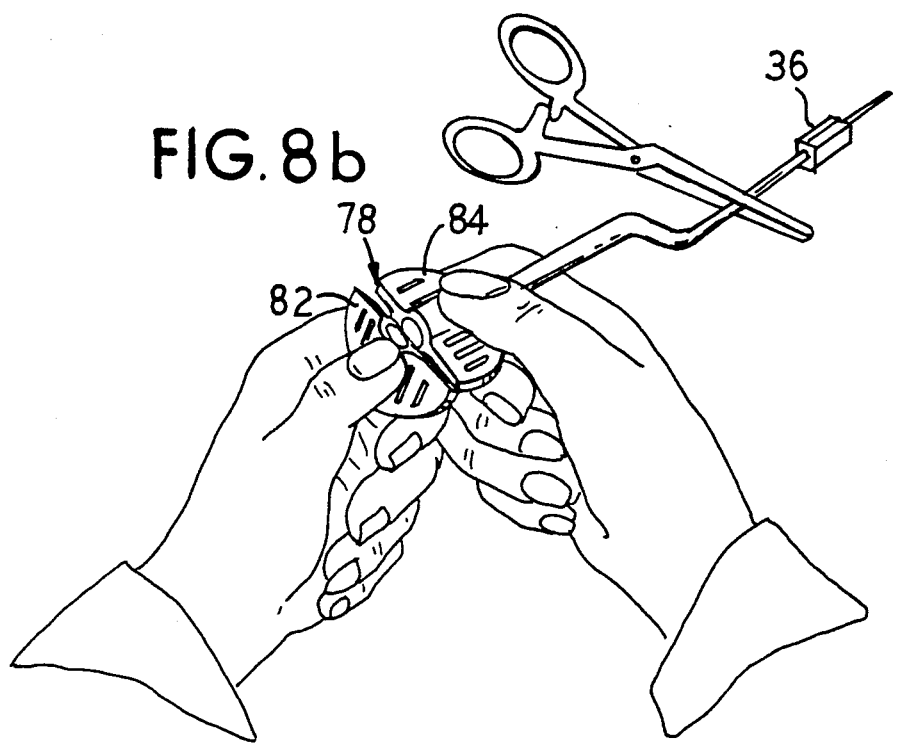
FIG. 8b is a perspective view of the sampling member of FIG. 8a being manipulated.

FIG. 8b illustrates the wings 80 being used to break the sample member 78 open for insertion of a luer or other device (not shown).

FIG. 9a illustrates another embodiment of a sampling member 100. In this embodiment, the first tubular section 30 and the second tubular section 32 including the notch 50 are constructed identical to that shown in FIG. 6. However, attached on an outside of the first section 30 is a wing 102 having a trapezoidal shape. Attached on an outside of the second section 32 is a wall 104. Hingedly extending from opposite sides of the wall 104 are a first fork lever 106 and a second fork lever 108.

In the folded together condition illustrated in FIG. 9a, the first fork lever 106 is snapped together with the second fork lever 108, sandwiching the wing 102 therebetween and reinforcing the notch 50. The first fork lever has tines 110 which extend from the wall 104 slightly less than second tines 112 of the second fork lever 108 in the folded over condition. Thus, the first fork lever 106 snaps within the second fork lever 108.

As illustrated, the first fork lever 106 has head portions 114 and the second fork lever has barbed portions 116. When the first fork lever 106 is snapped within the second fork lever 108, the head portions 114 snap past, and are hooked by, the barbed portions 116 thus holding the first fork lever 106 and the second fork lever 108 together.

FIG. 9b illustrates the first fork lever 106 and the second fork lever 108 pried apart, by resiliently deflecting the barbed portions 116 in a direction away from the wall 104 to release the head portions 114 of the first fork lever 106. The first fork lever 106 and the second fork lever 108 are peeled backwards in a direction shown by the arrows 120a, 120b.

Arranged on an outside surface (outside in the condition of FIG. 9a) of the first fork lever 106 and the second fork lever 108 respectively are triangular anvil pieces 118, 119 respectively. With the first fork lever 106 and the second fork lever 108 peeled back, as illustrated in FIG. 9b, the anvil pieces 118, 119 pinch the sample tube 34 therebetween so that further squeezing of the first fork lever 106 and the second fork lever 108 together prevents flow through the sample tube 34.

The sampling member 100 has the circumferential notch 50 formed therethrough for making a frangible joint between the first tube section 30 and the second tube section 32 for separating the donor tube 26 and the first section 30 from the sample member 100. This procedure is shown in FIG. 9c wherein a bending movement by the handler separates the sample member 100.

As illustrated in FIG. 9d, the tube holder 58 having the male luer nozzle 68 can now be inserted into the second section 32 of the fitting 100. Thereafter, releasing squeezing pressure on the first fork member 106 the second fork lever 108 allows blood to flow into the tube holder 58 and into the test tube 69 as previously described.

Figure 10:
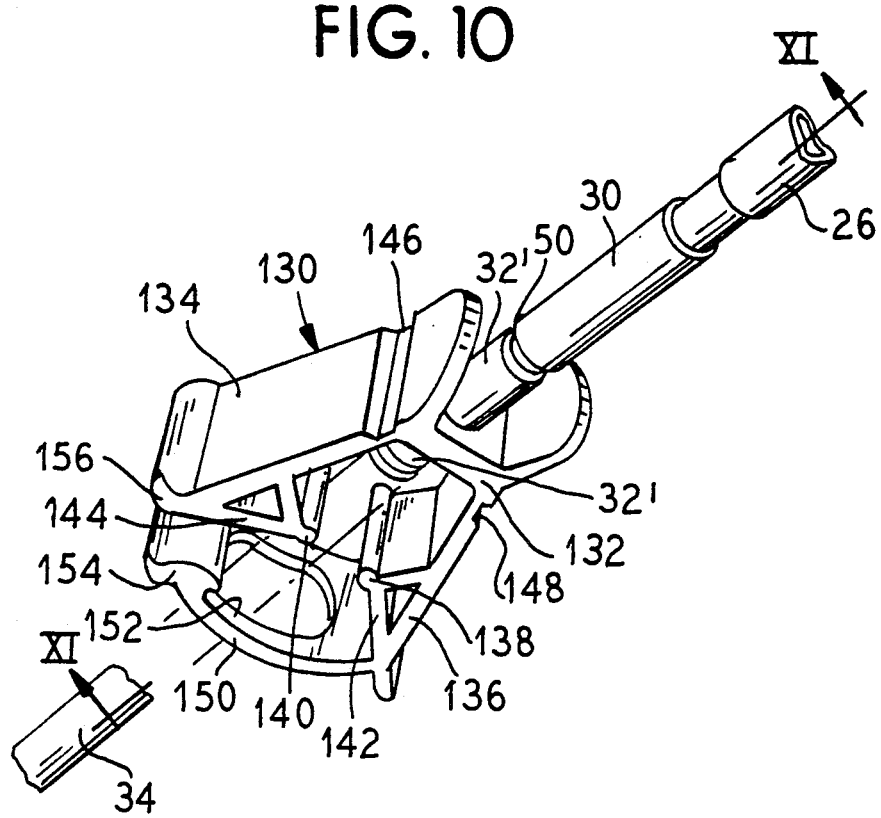
FIG. 10 is a perspective view of an additional sampling member according to the invention.

FIG. 10 illustrates a further embodiment of the sampling member 130. The sampling member 130 includes the first section as previously described with respect to FIG. 5 (first section 30) and a modified second section 32' with the notch 50 therebetween. The modified section 32' need not be provided with a port for the acceptance of a male luer nozzle.

Fixed to the second tube section 32' is a base 132. Extending from the base is a first wall 134, and a second wall 136. Extending inwardly of the two walls 136, 134 are two rounded bars 138, 140 extending inwardly from anvil structures 142, 144 respectively. The bars 138, 140 are aligned in order to squeeze the sample tube 34 therebetween as shown in FIG. 12a.

The first wall 134 and the second wall 136 have thinned walls or film hinges 146, 148 respectively in order to pivot the walls 134, 136 toward and away from each other. The second wall 136 has extending therefrom and toward the first wall 134, a back wall 150 having an aperture 152 therethrough and a hook piece 154 located at a distal end thereof. The first wall 134 has an inclined headpiece 156 extending at a distal end thereof.

Figure 11:
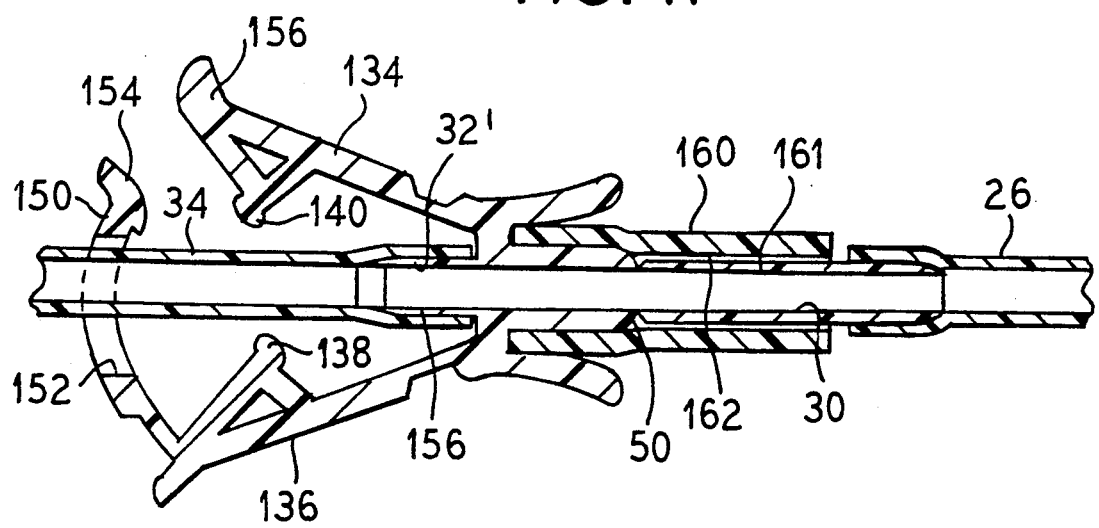
FIG. 11 is a longitudinal sectional view taken generally along line XI—XI of FIG. 10.

FIG. 11 illustrates the sampling tube 34 press fitted onto the second tube section 32' and bonded during steam sterilization. The sampling tube 34 in the illustrated embodiment, can be approximately 10 inches long leading to the needle 36. Also shown in FIG. 11 is a bushing 160, preferably PVC, which overfits a portion of the second tube section 32' and will be bonded thereto during steam sterilization.

The first tube section 30 receives the donor tube 26 which connects to the container 22. The tube 26 is press fitted onto the first tube section 30 and will be bonded thereto during steam sterilization. In a preferred embodiment, the first tube section and the second tube section 32' are polycarbonate.

Between the first tube section 30 and the bushing 160 are arranged longitudinal ribs 161 which hold the inner surface 162 of the bushing 160 away from the first tube section 30. This insures that the bushing 160 will not effectively bond to the first tube section 30 during steam sterilization.

The sample tube 34 extends from the second tube section 32' outwardly through the aperture 152 and onward to the needle 36.

FIG. 12a illustrates the sampling member 130 connected to a donor. However, before sticking the donor, the sampling member 130 is closed, i.e., the bars 138, 140 clamping the tube 34 are closed. This avoids draining anticoagulant after a needle cover (not shown) has been removed. The donor is then stuck, the bars 138, 140 released and the blood donation takes place.

When the donation is completed, the bars 138, 140 are squeezed together to close the tube 34 and the container 22 is separated as shown in FIG. 12a. The bars 138, 140 have been squeezed together and the head portion 156 has been moved to underlie the hook portion 154 which holds the two bars 138, 140 together with the sample tube 34 squeezed shut. Longitudinal ribs 161 are shown within the bushing 160.

The inlet tube 26 has been severed and clamps 56a, 56b have been installed to isolate the bag 22 from the tube 26 adjacent the sample member 130. This is described in more detail with regard to FIG. 7a.

As illustrated in FIG. 12b the notch 50 can be broken by bending. A portion of the tube 26 and the first section 30 can then be separated from the sample member 130, as shown in FIG. 12c. Separation of the first section 30 leaves a chamber inside the bushing 160 which contains no blood.

As illustrated in FIG. 12d the tube holder 58 can be inserted into the bushing 160 with the male portion 68 interfittable into a now opened end of the bushing 160. The insertion inside the bushing 160 can take place with no spillage of blood. The bars 138, 140 can be released to allow the flow of blood through the fitting and into the sample tube 69.

An evacuated tube can be used for collecting the blood sample or the sampling can take place by draining the blood from the open bushing 160 into open sample tubes or other means for collecting blood.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim as our invention:

1. A device for sampling blood from a blood donor, the device being in flow communication with a needle that is designed to receive blood from a source, the needle being connected to a tube leading to a blood bag, comprising:
   a tubular member, the tubular member having means for allowing flow communication with a collection tube for collecting a blood sample, the tubular member having a frangible joint for separating the tubular member into two pieces, one of the two pieces at the frangible joint including a luer port for connection of a luer adaptor thereto for establishing flow communication between said one of the two pieces having the luer port of the tubular member and an outside environment.

2. The device of claim 1, wherein the frangible joint comprises a reduced outer diameter of the tubular member.

3. The device of claim 1 further comprising portions positioned on opposite outside sides of the frangible joint for providing a gripping surface.

4. The device of claim 1 further comprising clamping means positioned upstream, with respect to blood flow through the tube, of the frangible joint.

5. A device for sampling blood from a blood donor, the device being in flow communication with a needle that is designed to receive blood from a source, the needle being connected to a tube leading to a blood bag, comprising:
   a tubular member, the tubular member having means for allowing flow communication with a collection tube for collecting a blood sample one end to a collection tube, the tubular member having a frangible joint for separating the tubular member into two pieces and establishing flow communication between a portion of the tubular member and an outside environment; and
   a tube clamping means positioned on the tube in juxtaposition to the frangible joint, and having opposite raised portions for squeezing the tube when the clamping means is oriented in a first position, and when oriented in a second position the tube clamping means bridges the frangible joint and supports the frangible joint from breaking.

6. The device of claim 5, wherein the clamping means comprises two forked lever arms each having two tines, the forked lever arms including the raised portions, the forked lever arms being hingedly mounted with respect to the tube on one side of the frangible joint pivotable about axes perpendicular to an axis of the tube, the forked lever arms pivotable from the first position into the second position, and when the arms are pivoted into the second position, the forked lever arms span the frangible joint on opposite sides of the tubular member, the forked lever arms interengaging to lock in the second position.

7. The device of claim 5 further comprising a finger tab portion positioned on an opposite side of the frangible joint from the clamping means, when the clamping means is in the first position.

8. The device of claim 1 further comprising a bushing surrounding the tubular section and positioned to span across the frangible joint, the bushing bonded to one side of the frangible joint and surrounding but not bonded to a respective other side of the frangible joint.

9. The device of claim 1 further comprising a clamping means positioned on a first side of the frangible joint, the clamping means comprising a plate member attached to a first side of the frangible joint and a first lever and a second lever each extending from the plate member in facing relationship, the first lever and the second lever having first and second raised sections extending inward toward each other from the first lever and the second lever respectively, the first lever having a plate portion extending at a distal end thereof toward the second lever, the plate portion having a hook thereon which is engageable to the second lever when the first lever and the second lever are directed toward each other and the first raised section is brought near to the second raised section, the plate portion having an aperture for passing a tube therethrough to the first section.

10. A medical device for installation inline into a fluid carrying tube, comprising:
    a tubular member having an axial channel therethrough, and a frangible joint provided at a location along the length of the tubular member for separating the tubular member into two pieces at the plane of said frangible joint, revealing a flow connection port at an opened end of one of said two pieces, and
    a clamping means connected to the tubular member and actuatable to squeeze shut the tube adjacent the tubular member, wherein the clamping means comprises a first lever and a second lever hingedly connected to the tubular member to pivot about axes perpendicular to an axis of the tubular member and positioned on opposite sides of the tube, the first and second levers having raised portions extendable toward the tube, the raised portions aligned to each other to compress the tube therebetween when the first and second levers are squeezed together.

11. The medical device of claim 10 wherein the tubular member comprises a conical cavity section adjacent the frangible joint openable once the tubular member is separated into two pieces, the conical cavity section shaped to accept a male luer.

12. The medical device of claim 10 wherein the tubular member and the clamping means comprise a unitary piece of molded plastic.

13. The medical device of claim 10 further comprising a bushing installed around the tubular member and sealed against one piece of the tubular member and extending over and along a respective opposite piece of the tubular member.

14. A medical device for installation in-line into a fluid carrying tube, comprising:
    a tubular member having an axial channel therethrough, and a frangible joint provided at a location along the length of the tubular member for separating the tubular member into two pieces; and
    a clamping/supporting means mounted to the tubular member and actuatable in a first position to clamp the tube at a location adjacent the tubular member, and actuatable into a second position to span the frangible joint and self-lock in the second position.

15. A method for sampling undiluted blood from a blood donor comprising the steps of:

providing a tube communicating from a blood drawing needle to a blood collection bag;

providing a device comprising a frangible joint in line with the tube between the needle and the blood bag, the frangible joint, once separated, providing a port shaped to receive a male luer adaptor, the port arranged on a side of the frangible joint thus remains flow connected to the needle once the frangible joint is separated;

sticking the needle into the donor;

collecting blood from the donor into the blood collection bag through the tube and the device;

clamping the tube between the device and the needle; breaking the frangible joint;

inserting a male luer adaptor into the port;

flow connecting said male luer adaptor to an alternate collecting site; and unclamping the tube to provide blood flow from the needle to the alternate collecting site.

16. The method of claim 15 wherein said step of flow connecting said male luer adaptor is further characterized in that said alternate collecting site is a tube for sampling blood.

* * * * *